United States Patent [19]

Hale et al.

[11] 4,096,047
[45] Jun. 20, 1978

[54] ELECTROANALYTICAL TRANSDUCERS

[75] Inventors: John Martin Hale, Geneva; Eugen Weber, Hinwil, both of Switzerland

[73] Assignee: Orbisphere Corporation, Wilmington, Succursale de Collonge-Bellerive, Collonge-Bellerive, Switzerland

[21] Appl. No.: 773,163

[22] Filed: Mar. 1, 1977

[30] Foreign Application Priority Data

Mar. 12, 1976 Switzerland .................. 3076/76

[51] Int. Cl.² .................... G01N 27/30; G01N 27/46
[52] U.S. Cl. ............................. 204/195 P; 204/195 R
[58] Field of Search ........... 204/195 R, 195 P, 195 S, 204/1 T; 324/29

[56] References Cited
U.S. PATENT DOCUMENTS

| 2,208,023 | 7/1940 | Ellis | 204/195 R X |
| 3,166,485 | 1/1965 | Lloyd | 204/1 T |

*Primary Examiner*—G. L. Kaplan
*Attorney, Agent, or Firm*—Kenyon & Kenyon, Reilly, Carr & Chapin

[57] ABSTRACT

Electroanalytic transducers for electrochemical analysis of chemical substances are disclosed. The transducers are of the type which include electrodes contacting an electrolyte solution. In accordance with the method and apparatus of the invention, means insulating an electrode are held in a mutually pressing engagement over preselected portions of the electrode to insulate that portion from the electrolyte and prevent creep of the electrolyte between the insulating means and the preselected portions. Thus, the surface area of the electrode exposed to the electrolyte is maintained substantially constant during the service life of the transducer. In a preferred embodiment, sensor or working and counter electrodes are coaxially mounted and circumferentially coaxially separated by annular insulating means. Spring means urge the inner coaxially mounted electrode and the annular insulating means together so that only the surface of the cross-sectional end of the inner electrode is exposed to electrolyte. Thus, a working or sensing surface area of the electrode exposed to electrolyte may be maintained substantially constant during service.

39 Claims, 5 Drawing Figures

ELECTROANALYTICAL TRANSDUCERS

BACKGROUND OF THE INVENTION

1. Field of the Invention

The present invention relates to electroanalytic transducers used for quantitative electrochemical analysis of chemical substances and more particularly to apparatus and a method for insulating preselected portions of transducer electrodes from electrolyte.

2. Description of the Prior Art

Transducers of the type used for quantitative electrochemical analysis of chemical substances are well known in the art and generally include a working or sensing electrode having a defined, or electroanalytically effective, surface portion for contact with an electrolyte and an insulator that limits the exposed surface of the working electrode. For amperometric analytical operation, the working electrode in a transducer-type cell arrangement is polarized by a constant DC voltage to furnish a current whose steady state magnitude is proportional to the activity of the chemical substance of interest. Transducers of this type and their operation and uses are discussed in detail in the following illustrative U.S. Pat. Nos. 2,913,386, 3,071,530, 3,223,608, 3,227,643, 3,372,103, 3,406,109, 3,429,796, 3,514,658 and 3,622,488. Generally, these prior art transducers are electrochemical cells in which a suitable electrolyte contacts the working electrode, the counter electrode, and the insulator that separates the electrodes, and prevents direct electric currents from flowing between the electrodes so that any current which is permitted to pass is ionic current in the electrolyte arising from electrochemical phenomena at the working electrode and the counter electrode. Important examples of this type of electrochemical transducer are the membrane enclosed polarographic devices which are widely used for the measurement of the concentrations of gases such as oxygen, chlorine and sulfur dioxide in a fluid, such as water, a gas mixture and the like. A recognized fault or deflect common to all conventional electrochemical transducers is the presence of an unwanted contribution to the total current that is unrelated to the activity of the substance to be analyzed. This unwanted contribution is manifested in two ways during operation: as an excess exponentially decaying transient contribution initiated by switching the current on; and as a residual contribution which remains after the chemical substance of major interest is excluded from the system. These defects restrict the application of the transducer to a range of activities of the chemical substance to be analyzed which are greater than a minimum detectable limit, and introduce a waiting period for the signal to stabilize before measurements may be begun. Furthermore, it is commonly observed that the magnitude and period of stabilization of the transient signal and the size of the residual current increase with the age of the transducer.

In accordance with the present invention, it has been found that an essential and common cause of the aforementioned defects of prior art transducers is a penetration phenomenon characterized by unintended contact of portions of the working electrode with the electrolyte. Thus, those portions not intended for contact with the electrolyte become exposed to interaction with the electrolyte or constituents thereof, thus changing the electroanalytically effective surface portion of the working electrode and forming an uncontrolled "gap" or access channel. While not wishing to be bound by any theory, this phenomenon can be explained by an unexpectedly strong tendency of a liquid electrolyte or electrolyte portion including the ions present or formed during operation, for example, water with or without the electrolytic solute in the case of aqueous electrolytes, to creep into the junction or interface between metal and common insulating materials. The charged state of the electrode during operation of the transducer does increase the creep tendency of electrolyte penetration into the metal/insulator interface. As a consequence of this penetration, the available area of the electrode which can interact with the electrolyte and at which electrode reactions can take place may be greatly extended, even though the additional area may be accessible only through, a highly resistive electrolytic conductor. Double layer capacity charging of the extended electrode surface will occur, and the charging current flows through the electrolytic resistance of the uncontrolled gap or access channel, thus increasing the magnitude of the unwanted current contribution in prior art transducers. It is important to note that the aforementioned prior art defects are present even in transducers in which the electrode/insulator junction commonly is assumed to be impermeable to liquids, for example, a strong adhesive bond obtained by cementing or curing a thermosetting polymer in contact with the metal electrode. Attempts to improve the adhesive bond, for example, by using polymers with polar groups and other methods for improving adhesive bonding, fail to show a significant improvement.

In accordance with the present invention substantial improvements in the performance of electroanalytical transducers are obtained over the prior art.

SUMMARY OF THE INVENTION

According to the present invention, contact between an electrode and insulator comprising an electrode/insulator interface in an electroanalytical transducer is maintained under pressure over the area of the interface. Preferably, the pressure is of predetermined magnitude and maintained substantially constant. In amperometric electrochemical transducers of the invention, a conventional cemented or adhesive type junction is replaced by an electrode/insulator interface kept under the impact of a force per unit of interface area, preferably predetermined and essentially constant. According to a preferred embodiment of the invention, the interface of the working electrode and the insulator accessible to, or intended for, contact with the electrolyte maintained in a pressing engagement. Thus, the interface which is subject to electrolyte penetration in the operation of the transducer is not a cemented or adhesive type joint. The term "pressing engagement" is used to define a solid/solid sealing interface in which the sealing effect is due to an "external" force, i.e., a force not inherent in the constituent electrode/insulator solids, thus excluding mere adhesive bondings of the type obtained by conventional cementing methods.

In disclosed embodiments of the invention, pressing engagement of solid/solid functions are accomplished by valve/valve seat arrangements in pressing engagement, for example, under the effect of mechanical energy storing means such as, for example, a spring. In transducers according to the invention, a portion of the working electrode is, for example, shaped as the valve portion and a portion of the adjacent insulator body is shaped to form a matching valve seat, and the valve and valve seat portion are pressingly interconnected. It has been found according to the invention that such a pressing engagement surprisingly permits an effective counteraction against uncontrolled electrolyte penetration which is far better than conventional cemented bonds and that the performance of a transducer that, according to the invention, does include this feature will improve with the magnitude of the force applied in the pressing engagement so that virtually any chosen specification of practical importance can be met.

It will be apparent that the strength properties of the materials involved in the pressing engagement, i.e., the contact portion at least of the working electrode as well as the contact portion at least of the insulator, including such time-dependent strength properties as creep resistance, will become a factor limiting maximum contact pressures that can be achieved in the pressing engagement of the insulator/electrode interface. However, substantial improvements can be achieved well below such maximum pressures. As the mechanical properties of a material depend upon temperature, it is understood that any specific mechanical properties given herein are based upon normal temperatures of operating electroanalytical transducers, i.e., temperatures in the broad range of from about $-50°$ C to about $200°$ C depending upon the nature of the electrolyte. A range of from about $0°$ C to about $150°$ C is a preferred operating range, with a range of from about $15°$ C to about $30°$ C being even more preferred for many purposes.

It has been further found according to the invention that specific contact forces, i.e., pressures of contact at the interface (for example in $kg/mm^2$), well below the upper limit that would be permissible for many conventional insulators will provide the above-described advantages of reducing both the exponentially decaying transient contribution initiated by switching the current on and the residual contribution that remains even in the absence of the chemical substance of interest. In accordance with the invention, these advantages are achieved at pressures greater than about $0.1 \ kg/mm^2$, and preferably greater than about $0.5 \ kg/mm^2$. For practical reasons including cost of materials and production, an upper limit of the pressure of contact at the interface will be about $300 \ kg/mm^2$. The specific contact pressure chosen in the broad range of from about $0.5 \ kg/mm^2$ to about $300 \ kg/mm^2$ will, in many instances, be determined by the strength properties including creep resistance of the insulator.

Many conventional insulator materials that are desirable in view of electrical properties, stability against the electrolyte with or without applied current and against the direct and indirect effects of the substances analyzed will operate satisfactorily at pressures of contact which, expressed in $kg/mm^2$, are in the range of up to about 95% of the yield or tensile strength of the insulator material, also expressed in $kg/mm^2$. Such insulators, include for example, insulators from the broad class of organic polymers including both thermoplastic and duroplastic species. For example, many advantageous organic polymers that are inherently suitable as insulators because of their electrical and chemical properties can be used at pressures of contact in the range of from about $0.5 \ kg/mm^2$ to about $4 \ kg/mm^2$. The pressures of contact between the insulator and the electrode within the above-defined ranges need not be maintained over the entire interface of the working electrode and the insulator. In general, it will be sufficient if a sealingly effective portion of the interface near the electrolyte contacting end of the interface is maintained in pressing engagement, i.e., at pressures of contact of about $0.1 \ kg/mm^2$.

According to a preferred embodiment, the transducer includes an arrangement for effecting, i.e., both causing and maintaining, a predetermined and substantially constant pressure of contact at the sealingly effective portion of the electrode/insulator interface. Such an arrangement may include a resilient element, for example, a spring, one operative end of which is in direct or indirect engagement with the working electrode while its other operative end is in direct or indirect engagement with the insulator body that determines the electroanalytically effective surface of the working electrode, i.e., that surface portion exposed to the electrolyte when the transducer is in an operative assembly including a counter electrode and an electrolyte.

Typical examples of materials for the working electrode used in transducers according to the invention include numerous metals or metal alloys conventional in the transducer art, for example, inert (relative to the electrolyte and electrolysis products) metals selected from the nobel metals, such as gold, platinum, palladium and iridium. High grade stainless steel is another example. It is to be noted that it is the surface of the working electrode exposed to electrolyte and electrolytic decompositon products that should be substantially inert and non-consumable. Thus, it may be advantageous for commercial reasons if only the exposed surface of the working electrode is made of one of the above materials while the core and/or non-exposed portions of the electrode may be of a less expensive structural material such as nickel, chromium or copper.

Typical examples of suitable insulator materials for the electrode/insulator interface of transducers according to the invention include such materials as organic and inorganic insulating materials from the broad group of solid organic polymers, (thermoplastic or duroplastic), silicates, fused oxides, glasses, etc. Specific examples include cured epoxides, polypropylene, Nylon 66, polyethylene terephthalate, acrylics including polymethacrylic esters, polystyrene, polyvinyl chloride (unplasticized), high density polyethylene, polyvinylidene fluoride, polyvinyl carbazole, polyvinyl acetate, polysulfones, polycarbonates including polybisphenol carbonate, polyphenylene oxide, polyurethane, polyacetals including polyoxymethylene, various copolymers including those made of styrene and acrylonitrile or of styrene, acrylonitrile and butadiene, glass, quartz (fused silica), ruby, diamond, granite ceramics, ebonite, ivory, etc. Mixtures including composite materials such as polymers from the above classes with a disperse phase of a filler that may or may not have a reinforcing effect, for example, polyester or polyepoxide compositions with glass in particulate or fibrous form, may be used for forming the insulator portion or portions of the electroanalytical transducers according to the invention.

The general criteria for selecting suitable insulator materials according to the invention will be readily apparent to those skilled in the art in view of the disclosure and the basic requirements of (a) the insulating function, (b) the capacity to come into, and remain in, a sealing and pressing engagement with the working electrode and (c) preventing changes of both mechanical configuration and electrical properties under operating conditions of the transducer for the desired life of the components. As mentioned hereinabove, a high creep resistance in addition to the high strength requirement is preferred for the materials pressingly engaged at the electrode/insulator interface. At a continuous contact pressure in the preferred range of about 0.5 kg/mm$^2$ to about 4 kg/mm$^2$ some organic polymers may show well-known creep effects which are undesirable as deformation of the insulator with concurrent change of the electroanalytically effective surface portion of the electrode and/or the contact pressure at the critical electrode/insulator interface portion may occur. Therefore, high creep resistance is preferred to prevent changes of mechanical configuration and electrical properties, as mentioned, in view of the magnitude of the forces per unit of the critical electrode/insulator interface area and the effect of such forces on conventional insulators from the class of duroplastic or thermoplastic organic polymers.

Thus, when using such polymers for transducers, according to the invention, it is preferred that insulator material have a creep modulus of at least about 14 kg/mm$^2$. This modulus is defined as the ratio of the applied stress to the total (percentage or fraction) strain caused by the stress. For example, a material with a creep modulus of 14 kg/mm$^2$ would show about 7.15% compression under a 1 kg/mm$^2$ applied load; in other words, a low percentage compression value of the insulator under the impact of the sealingly effective contact pressure at the electrode/insulator interface is preferred for the insulator. Since the creep modulus of an organic polymer tends to decrease with time and temperature, the preferred creep modulus of insulators used at the interface of at least about 14 kg/mm$^2$ should exceed that value for the desired life of the components and for the entire working temperature range of the transducer. The possibility of an interaction of the insulator with the electrolyte, for example, water or non-aqueous solvent, is pointed out and should be kept in mind when selecting the insulator. However, specific criteria of solvent or water stability of polymers are well known in the art and need not be herein discussed in detail. As an illustration of some preferred commercially obtainable insulator materials, polyacetales show a room temperature creep modulus after one hour of about 280 kg/mm$^2$ and after 10$^4$ hours of about 110 kg/mm$^2$. Also, commercial-type plastics from the groups of polysulfones, polycarbonates, polyphenylene oxide, poly-(styrene acrylonitrile) or "SAN" resins and poly(acrylonitrile butadiene styrene) or "ABS" resins show high creep modulae of well above 14 kg/mm$^2$ for 10$^4$ hours at most measuring temperatures of interest and in the presence of aqueous electrolytes.

As indicated hereinabove, transducers for quantitative electroanalysis will generally include a counter electrode. Arrangement of compounds and selection of suitable materials are not critical and normal structures and materials disclosed in the aforementioned U.S. patents may be used. For example, tube-like structures made of silver which enclose the working electrode and insulator assembly as described hereinabove may be used, provided, of course, that the critical pressing engagement of the working electrode and the insulator is effective. On the other hand, the interface between the counter electrode and insulator is not critical and this junction may, or may not, be arranged in the pressing relation described hereinabove. An increase of the surface exposed to the electrolyte of the counter electrode by electrolyte penetration into the insulator/counter electrode interface does not have the same consequences as a change of the electroanalytically active surface of the working or sensing electrode. However, it is preferred that both the working electrode and the counter electrode are in pressing engagement as described hereinabove.

With respect to the electrolyte required for operation of a transducer, reference is made to the aforementioned U.S. patents. Electrolyte composition and concentrations for various purposes of analysis and analytical environment are well known in the art. It is to be noted that transducers according to the invention are operative and advantages thereof obtained both with aqueous and non-aqueous electrolyte. Suitable electrolytes of the aqueous and non-aqueous type with or without additives such as buffers are standard and depend upon the nature of the chemical substance that is analyzed. Solutions of alkali metal halides and/or hydroxides and/or nitrates in aqueous or non-aqueous media are mentioned for purposes of illustration and not limitation. Examples of non-aqueous solvents for electrolytes include organic mono- or polyalcohols, ketones, esters, amides, etc. It is understood that the operating conditions of the transducers (for example, below 0° C or above 100° C) are an essential parameter in selecting a suitable solvent for the electrolyte. The electrolyte concentration may vary within wide limits, for example, from a fraction of a mole/liter to several moles/liter. In general, typical resistivities of the electrolyte may range from about 10 to about 10,000Ω cm. The electrolyte may include conventional additives for lowering the freezing point, for changing the viscosity, for improved melting, etc. It is also pointed out that while liquid electrolytes are most commonly used, transducers according to the invention may be used with gel-type electrolytes or "solid electrolytes", i.e., solid electrolyte pads or carriers containing the electrolyte in an adsorbed form.

It is a generally accepted practice in the electroanalytical art to provide a cell with a permeable or membrane-type wall. Transducers operating in that manner will generally comprise an electrolyte-receiving container portion sealed with a membrane that is impervious to the electrolyte but is permeable to a gas. Transducers of this type may be used, for example, for the analysis of oxygen in a gaseous or liquid stream and have a membrane made of, for example, polytetrafluoroethylene. Other similar systems may be used to sense or quantitatively measure sulfur dioxide, hydrogen sulfide, free halogen, for example chlorine or fluorine, etc.

Since the operation of the transducer in a membrane-type cell is influenced by the thickness of the semipermeable membrane, it is generally preferred in accordance with the invention to use very thin membranes, for example, having a thickness of not more than about 20 micrometers. Membranes with thicknesses in the range of about 10 micrometers to about 20 micrometers are most preferred, particularly if made of a high-tenacity polymer, for example, polytetrafluoroethylene. Oriented polymer membranes may also be suitable or may even be preferred.

These and other aspects of the present invention will be more apparent from the following description of the preferred embodiments when considered with the accompanying drawings and appended claims.

BRIEF DESCRIPTION OF THE DRAWINGS

The present invention is illustrated by way of example and not limitation in the figures of the accompanying drawings in which like references refer to like parts and in which.

DESCRIPTION OF THE PREFERRED EMBODIMENTS

Figure 1:
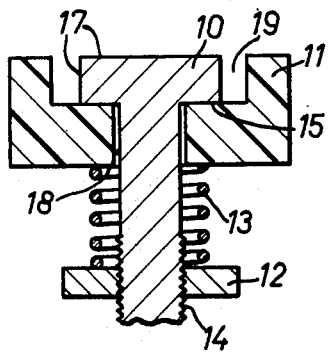
FIG. 1 is a diagrammatic cross-sectional view of an electrode/insulator arrangement in a transducer according to the invention.

In FIG. 1, working electrode 10 is shown in a pressing and sealing engagement with insulator 11 according to the invention in which spring 13 is arranged between insulator body 11 and a ring 12 so as to generate and maintain a minimum pressure of contact at interface 15. It is understood that a device for storing energy other than spring 13 may be used. While ring 12 is shown as an adjustable means for tensioning spring 13 in the form of a threaded nut adjustably positioned along the threaded portion 14 of electrode 10, such a continuously adjustable arrangement is not a critical arrangement but is preferred. On the other hand, it is essential according to the invention that sealingly effective pressure between electrode 10 and insulator 11 is provided at interface 15 as described hereinabove. This interface pressure is assumed to be critical according to the invention for counteracting penetration of an electrolyte provided within an elecrolyte-receiving portion 19 so as to prevent change of the electrolyte-exposed and thus electroanalytically effective surface portion 17 of electrode 10 which functions as the working electrode of a cell assembly also comprising a counter electrode which is not shown in FIG. 1. The electrical circuitry and electronic devices required for operation of the transducer are not shown in the drawings. However, detailed discussion is not required herein since suitable circuit arrangements including connections of the electrode with a source of constant voltage as well as amperometric means including amplifiers and current-measuring apparatus are well known in the art of electroanalysis. Specific examples of suitable circuits are shown in the aforementioned U.S. patents.

Returning to FIG. 1, it is pointed out that electrode 10 is not required to be cemented, i.e., adhesively bonded, to the insulator but that sealing interconnection at interface 15 is effected solely by a pressing engagement of insulator 11 and electrode 10 caused by the force exerted by the compressed spring or a similar energy-storage means. As described hereinabove, only the portion of the interface provided between electrode 10 and insulator 11 near the electrolyte-exposed end of the interface where electrolyte penetration need be counteracted, according to the invention, need be in pressing engagement by contact pressures in the magnitudes as described hereinabove. Gap or space 18 is shown in an enlarged manner, it being understood that in this area of adjacent electrode/insulator surfaces, no electrolyte is present in normal operation. The working electrode and adjacent insulator configuration shown in FIG. 1 may, for example, be arranged within a metal tube or the like (not shown in FIG. 1) which forms the recessed counter-electrode so that the electrolyte provided at 19 will be in contact with both the working and counter electrodes. As the counter electrode/insulator interface is less critical with respect to electrolyte penetration, the structure of FIG. 1 may be cemented to, or otherwise secured within, a surrounding metal tube (not shown).

Figure 2:
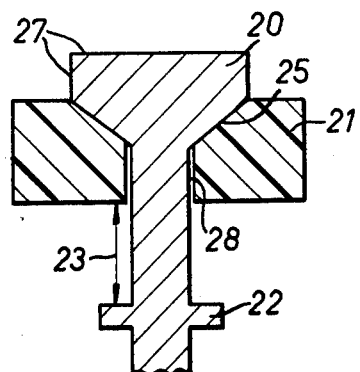
FIG. 2 is a diagrammatic cross-sectional view of a modification of the arrangement shown in FIG. 1.

A sealing interface arrangement according to the invention somewhat modified from that of FIG. 1 is shown in FIG. 2 and includes a working electrode 20 and an insulator 21. The electroanalytically effective surface portions 27 of electrode 20 are intended for contact with an electrolyte and any penetration of electrolyte into the electrode/insulator interface 25 will, as described hereinabove, be disadvantageous. This penetration is prevented in a manner similar to that set forth with respect to FIG. 1. Among the coaxial or cylindrically symmetrical configurations shown in FIGS. 1–5, FIGS. 2, 4 and 5 show a preferred shape of the interface, i.e., a conical or frustro-conical interface configuration, and FIGS. 2 and 5 are examples of preferred valve/valve seat arrangements for the insulator/working electrode interface for transducers according to the invention. Referring now to FIG. 2, the electrode portion of interface 25 is shaped and may be considered as a "valve" means while the insulator portion of interface 25 is shaped and may be considered as the corresponding "valve seat" means. In a manner similar to that shown in and described in connection with FIG. 1, an energy storing device, such as a spring, is provided to cause a force indicated by the double arrow 23 to act between insulator 21 and a force-engaging portion 22 of, or interconnected with, working electrode 20. Again, a major portion of adjacent electrode/insulator surfaces as illustrated by gap 28 is not intended for pressing contact and the end of interface 25 near said gap is the one not intended to be exposed to contact with an electrolyte. The contact pressure generated at the interface 25 will be selected as described hereinabove to counteract electrolyte penetration. Conventional surface finishing of the electrode and insulator portions at the sealingly effective interface portion may be provided to further prevent electrolyte leakage while the contact at the interface is maintained as described hereinabove. Such finishing is, of course, more important if rigid insulator materials such as ceramics, glass and the like materials are used for the insulator component at sealing interface portions 15, 25 and 551 (FIG. 5).

Figure 3:
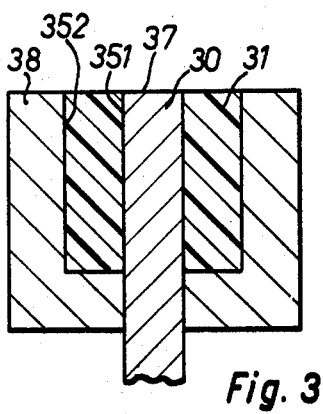
FIG. 3 is a diagrammatic cross-sectional view of another electrode/insulator arrangement according to the invention.

While the force effective in the embodiments of FIG. 1, 2 and 5 for generating the required contact pressure at the insulator/working electrode interface is applied in what can be said to constitute an "axial" manner, for example, by using axially compressible spring means, other manners of applying force may be used. In the embodiments shown in FIGS. 3 and 4 the force is applied in a "radial" (relative to the longitudinal axis of the working electrode) manner. In FIG. 3, for example, working electrode 30 (with its electroanalytically effective surface portion being defined by its circular front face 37) is surrounded by an insulator 31 so as to provide a sealingly effective interface 351 in pressing engagement of the adjacent parts at or near the electrolyte-exposed end of that interface around front face 37. An insulator suitable for that purpose will have some resilience, or spring effect, displaying tensile rather than compressive strain so as to be capable of sustantially maintaining the contact pressure required at the sealingly effective portion of interface 351 once the surrounding rigid body 38 is caused to compress insulator 31. Body 38 may be a second insulator portion and counter-electrode (not shown) is added as described hereinabove in connection with FIG. 1. Alternatively, rigid body 38 may be made of a metal suitable as the counter-electrode if an insulator portion (not shown) is provided between the working electrode 30 and body 38. In such an embodiment both the interface 351 between working electrode 37 and insulator 31 as well as the interface 352 between body 38 acting as a counter-electrode and insulator 31 could be kept in a sealingly effective engagement at or near their electrolyte-exposed portions. For example, an electrolyte layer (not shown) might be provided at the upper faces of components 30, 31 and 38 which would constitute, or be part of, an electrolyte-receiving container portion of the type suitable for electroanalytical operation of an amperometric cell structure.

Figure 4:
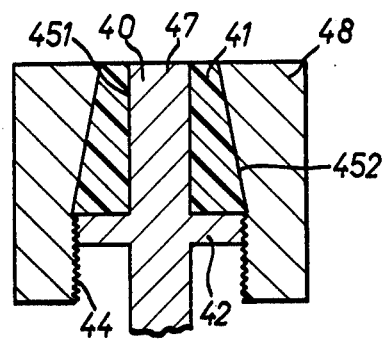
FIG. 4 is a diagrammatic cross-sectional view of a modification of the electrode/insulator arrangement shown in FIG. 3.
Figure 5:
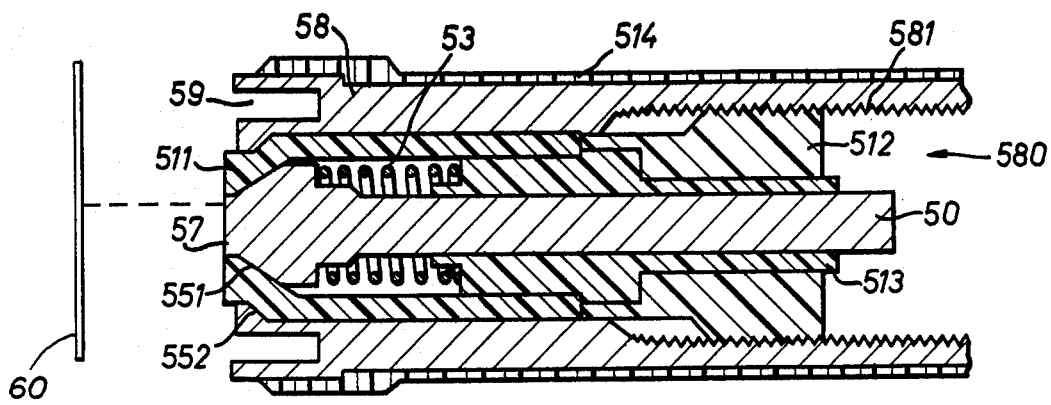
FIG. 5 is a semi-diagrammatic cross-sectional view of the head portion of a preferred embodiment of a transducer structure according to the invention.

Referring to FIG. 4, a modification of the embodiment for generating the desired contact pressure near the electrolyte-exposed interface by radially acting forces is shown. A mechanical chuck is formed by a rigid body 48 whose internal cavity or recessed portion receives working electrode 40 and a compressible insulator 41. A threaded part 44 is arranged within the internal cavity of body 48 and electrode 40 is provided with, or operatively connected to, a threaded portion 42. By displacing the threaded portion 42 along thread 44, the insulator 41 will be compressed and caused to pressingly engage interface 451 between electrode 40 and insulator 41 on one side, and interface 452 between body 48 and insulator 41 on the other side. Assuming that an electrolyte layer (not shown) is provided in contact with the electroanalytically effective surface portion 47 of electrode 40, the energy-storing effect of the compressed insulator 41 is used to maintain the desired contact pressure at or near the electrolyte-exposed portion of insulator/electrode interface 451. As described in connection with FIG. 3, rigid body 48 may be an insulator or it may be made of metal and serve as the counter electrode of an electroanalytical cell assembly provided electrical insulation (not shown) is maintained between body 48 and working electrode 40, for example, by using a rigid insulator for the threaded portion 42. While a mechanical chuck is shown in FIG. 4, it is understood that hydraulic pressure generation and transmission is within the scope of the present invention and that hydraulic-type chuck structures may be used to cause and maintain the required pressure of contact at or near the electrolyte-exposed portion of the insulator/working electrode interface.

FIG. 5 illustrates a preferred embodiment of the head portion of an electroanalytical transducer according to the invention. A working electrode 50 (cathode) whose electroanalytically effective surface portion 57 is made, for example, of gold is encompassed by a first insulator portion 511. A second insulator portion 512 is provided with an external thread for engagement with a correspondingly threaded part 581 of a counter electrode 58 (anode), made, for example, of silver and having an internal cavity 580 to receive and hold cathode 50 in pressing and sealing engagement at interface 551 with insulator 511. Spring 53, for example, a conventional axially compressible helix made of high-grade steel, is used as an energy storing device. The second threaded insulator 512 maintained in its relative position within the threaded portion 581 of cavity 580 of anode 58 may be in direct operative engagement and contact with the first insulator portion 511 and a third insulator portion 513 as shown, it being understood that in this fixed position spring 53 will have reached the desired final degree of compression and, thus, exert the desired force for pressing and sealing engagement of cathode 50 and insulator 511 at interface 551 near the electrolyte-exposed and analytically active surface 57. Interface 552 between counter electrode 58 and insulator 511 also will be in a pressing and sealing engagement generated and maintained by the compressed state of spring 53. The general front portion at the left side of FIG. 5 is intended to be exposed to an electrolyte and an annular reservoir 59 is provided for receiving such electrolyte. For operation, an end cap 60, for example, a thin film of polytetrafluoroethylene, will be arranged to cover the front portion and to hold the electrolyte. Insulating jacket 514 is provided with a radially extended end part for holding an O-ring (not shown) or the like around the end cap or film.

A specific example embodying the invention is set forth below. This example is illustrative and is not to be understood as limiting the scope and underlying principles of the invention in any way.

EXAMPLE

A transducer for the detection of oxygen was constructed in accordance with FIG. 5 comprising a gold working electrode 50 (the cathode) of 2 mm effective diameter, insulator portions 511, 512 and 513 made of a commercial-type polyacetal and a silver counter electrode 58. A 1M potassium hydroxide electrolyte was provided for contacting both electrodes, and a 12 micrometer "Teflon" membrane was used to permit entry of oxygen into the cell mounted close to the intentionally exposed disc-shaped electroanalytically effective surface portion 57 of gold. Steel spring 53 was loaded by means of nut 512 so that the specific pressure on interface 551 of the gold cathode and insulator 511 was 2 kg/mm². When operating in air at 20° C, the transducer furnished a steady state signal of 2.2 uA. Upon immersion of the transducer in a 3% sodium sulfite solution, in order to exclude the possibility of entry of oxygen through the membrane, the current decayed to 20 nA in 12 seconds, and to 0.2 nA in 5 minutes. A sudden change of 0.2 volt in the voltage applied across the cell while the transducer was submerged in sodium sulfite solution, resulted in a current transient described by equation (1)

$$i_c = i_o \exp(-t/\tau) \tag{1}$$

in which $i_o = 5$ nA and $\tau = 50$ seconds. Analysis according to the formula for a transmission line presented above gave R = 60 MΩ and C = 2 uF. These results imply an average channel thickness between the working electrode and the polyacetal of about $3 \times 10^{-7}$ cm. The specified performance characteristics represent a major improvement over those of conventionally moulded transducers.

Equation (1) provides a simplified one-dimensional model of double-layer capacity charging of the type referred to hereinabove caused by electrolyte penetration into the interface between the working electrode and the adjacent insulator. This equation is the "telegrapher's" equation for conduction in a transmission line of finite length having distributed resistance R and capacitance C and shows that the charging current $i_c$ at an instant $t$ following a change $\Delta V$ of applied potential is given by equation (1). Generally, $i_o = 2 \Delta V/R$ and $\tau = RC/\pi^2$. The important result to be noted here is that the current $i_c$ is inversely proportional to the magnitude of the resistance R in the access channel and that the period of exponential decay $\tau$ should be proportional to the product of this resistance and the magnitude of the double layer capacitance C. In the operation of conventional transducers this capacitance typically is of the order of 20 microfarads per cm² of metal area.

In order to illustrate the magnitude of quantities for comparative purposes a calculation was made for the case of a working electrode in the form of a wire of length L(cm), radius r(cm) of which only one disc-shaped end is intentionally exposed to the electrolyte. It will be assumed that shrinkage of the insulator surrounding the cylindrical surface (corresponding with prior art transducer structures) allows penetration of the electrolyte into an annular space of thickness $x$(cm), ($x << r$). The resistance of an electrolytic conductor is given by the formula $$R = \frac{SL}{a} = \frac{SL}{2\pi r x}$$

where S is the specific resistance of the electrolyte and "$a$" the cross-sectional area of the conductor. In particular for a 1 molar potassium chloride solution, as a representative example of electrolytes used in electrochemical transducers, S is of the order of 10 ohm cm. Hence, a channel 1 cm long, of 1 micrometer thickness between an insulator and a cylindrical electrode of diameter 1 mm presents a resistance to ionic current flow of a magnitude of about 0.3 megohms. In this case a potential jump of about 1 volt would produce a double layer charging current transient described by an $i_o$ of about 10 microamperes and $\tau$ of about 0.6 seconds. Such a current is comparable in magnitude to the steady state signals produced by electrochemical transducers in relatively high concentrations of the chemical substance to be analyzed. In order that the charging current be negligible in comparison with the desired signal, it is necessary that the gap width $x$ be small, causing the channel resistance R to be high and the characteristic current to be less than a desired specified residual current.

It will be understood that according to the invention, an effective means of keeping the gap width $x$ small even upon prolonged operation of the transducer presents an important advantage over the prior art.

Electrode reactions occurring at the surface of a working electrode extended due to electrolyte penetration at the electrode/insulator interface are less amenable to theoretical treatment than is the double layer charging current, because the magnitude of the corresponding electrolysis current depends upon the nature and concentration of all electroactive substances initially present in the annular space. The simplest and most probable case is that of a substance present at concentration $C_o$ throughout the volume of the annulus which is non-electroactive before application of the polarizing potential to the electrode but is electroactive at the fully charged electrode. A simplified theoretical model of this system results in the equation (2):

$$i_F = 2\pi r x \frac{nF\,C_o\Delta V}{St} \tag{2}$$

In addition to the symbols defined previously, $n$ is the number of electrons involved in one mole of electrode reaction and F, the faraday, is the number of coulombs of electricity on one mole of electrons. Choosing the magnitudes of the parameters mentioned previously and $C_o = 10^{-6}$ moles ml$^{-1}$ it is found that this faradaic current contribution amounts to 0.6 uA at 100 seconds after closing the circuit. Furthermore, a rather slow rate of decay is expected for this current so that it can feasibly appear to an observer as a steady state residual current. Assuming that this contribution to the excess current, too, is proportional to the thickness of the annular space, it follows that the insulator/working electrode interface according to the invention provides substantial improvements in the performance of electrochemical transducers.

In order to assess electrolyte penetration on the basis of thermodynamic theories of capillary and adhesion for an aqueous electrolyte, it is apparent that water tends to penetrate between two surfaces initially in contact if the free energy change accompanying this process is negative. For unit area of the interface, this free energy change is given by the Dupre equation (3)

$$W_A = \gamma_{1W} + \gamma_{2W} - \gamma_{12} \tag{3}$$

$W_A$ is known as the work of adhesion and the $\gamma$'s are interfacial tensions. Subscripts 1 and 2 refer to the two solid walls and W to the water. It is well known that the surface tension of a solid against vacuum is lowered by contacting the solid with any other medium because of molecular interactions across the interface. As a general rule, the surface tensions of metals ($\sim$500 ergs/cm²) and are much greater than those of insulators ($\sim$50 ergs/cm²) and the lowering of the surface tensions of a metal produced by contact with a solid insulator is greater than that produced by contact with water. A complication is that the interfacial tension between a metal electrode and an aqueous solution is further lowered by the presence of a net charge on the electrode surface. Hence, the force driving water into the junction between an electrode and an insulator is greater when the electrode bears a surface charge than when it is uncharged. It must be kept in mind that the Dupre equation represents a somewhat idealized situation as far as the initial contact between two solid bodies is concerned. In practice, solid surfaces are rough to a certain extent and equation (4) would be more accurate:

$$W_A^1 = \gamma_{1W} + \gamma_{2W} - \gamma_{12} - (1-\theta)(\gamma_{1A} + \gamma_{2A}) \tag{4}$$

where $\theta$ represents the fraction of the total surface area where true contact occurs and the subscript A refers to air. Surfaces would be considered separated by an air gap, in this context, if the gap between them exceeded about $10^{-7}$ cm. Since $\gamma_{12} < \gamma_{1A} + \gamma_{2A}$, $W_A^1$ is smaller than $W_A$ and water penetration is therefore more likely to occur than would be concluded on the basis of the unmodified Dupre model.

When an extraneous force is applied normal to the interface between two solids, additional work needs to be expended to separate these surfaces. For unit area of interface, therefore, the total work required to separate the surfaces and to introduce a film of water between them is defined by equation (5)

$$W_t = \gamma_{1W} + \gamma_{2W} - \gamma_{12} - (1-\theta)(\gamma_{1A} + \gamma_{2A}) + (P)(x) \quad (5)$$

where P represents an applied pressure and $x$ is the average distance through which the surfaces are separated. From this, it is again concluded that the thickness of an intervening layer of aqueous electrolyte at the electrode/insulator interface may be effectively decreased by a suitable choice of the magnitude of the effective component of the force producing the contact pressure at the interface.

Thus, theoretical analysis confirms the improvements in transducers according to the invention.

The advantages of the present invention, as well as certain changes and modifications of the disclosed embodiments thereof, will be readily apparent to those skilled in the art. It is the applicants' intention to cover by their claims all those changes and modifications which could be made to the embodiments of the invention herein chosen for the purpose of the disclosure without departing from the spirit and scope of the invention.

Protection by Letters Patent of this invention in all its aspects as the same are set forth in the appended claims is sought to the broadest extent that the prior art allows.

What is claimed is:

1. A method for preventing contact by an electrolyte of selected portions of an electrode not intended to be contacted by the electrolyte in an amperometric electroanalytical transducer comprising contacting at least a part of the surface of said electrode portions with an insulator adapted to seal said selected portions of said electrode against contact with said electrolyte, maintaining the insulator and the electrode in mutually pressing engagement at a pressure of greater than about 0.1 kg/mm² at the interface thereof.

2. The method of claim 1, wherein the insulator and the electrode surface portions are maintained under substantially constant pressure.

3. The method of claim 1, wherein pressure is maintained in said pressing engagement of between about 0.5 kg/mm² and about 4 kg/mm².

4. The method of claim 1, wherein pressure is maintained in said pressing engagement of between about 0.5 kg/mm² and about 300 kg/mm².

5. The method of claim 1, wherein said pressing engagement is obtained and maintained by external mechanical energy storage means.

6. The method of claim 1, wherein the insulator and the electrode surface portions are coaxially arranged and maintained in the mutually pressing engagement.

7. The method of claim 6, wherein the insulator and the electrode surface portions are coaxially arranged as a valve and valve seat to form said interface.

8. The method of claim 1 and using a creep-resistant material for the insulator.

9. The method of claim 1 and using a material for the insulator having a creep modulus of at least about 14 kg/mm².

10. The method of claim 1, wherein pressure is maintained in said pressing engagement of up to 95% of the strength of the insulator.

11. The method of claim 1, wherein said pressing engagement is obtained and maintained by the application of axial force.

12. The method of claim 1, wherein said pressing engagement is obtained and maintained by the application of radial force.

13. In an amperometric electroanalytical transducer comprising an electrode and an insulator for preventing contact by an electrolyte of selected portions of the electrode, the improvement comprising means for maintaining surface portions of an insulator and at least part of the surface of said selected portions of the electrode in mutually pressing engagement at a pressure of greater than about 0.1 kg/mm² at the interface thereof.

14. The improvement of claim 13, wherein said means maintains the insulator and electrode surface portions under substantially constant pressure.

15. The improvement of claim 13, wherein said means maintains a pressure between about 0.5 kg/mm² and about 4 kg/mm² between the insulator and electrode surface portions.

16. The improvement of claim 13, wherein said means maintains a pressure between about 0.5 kg/mm² and about 300 kg/mm² between said insulator and electrode surface portions.

17. The improvement of claim 13, wherein said means comprise mechanical energy storage means.

18. The improvement of claim 17, wherein said mechanical energy storage means comprises spring means.

19. The improvement of claim 17, wherein the insulator is resilient and said mechanical energy storage means comprise means for deforming the insulator.

20. The improvement of claim 13 wherein the insulator and electrode are coaxially arranged and said means maintains said insulator and electrode surface portions of the coaxially arranged insulator and electrode in the mutually pressing engagement.

21. The improvement of claim 20 wherein the electrode is valve-shaped and the insulator is valve-seat configured proximate said interface of the insulator and electrode.

22. The improvement of claim 13 and further comprising a creep-resistant insulator.

23. The improvement of claim 13 and further comprising an insulator having a creep modulus of at least 14 kg/mm².

24. The improvement of claim 13, wherein said means maintains a pressure up to 95% of the strength of the insulator between the insulator and electrode surface portions.

25. An amperometric electroanalytical transducer comprising insulating means including an insulator, at least one electrode having an electroanalytically effective surface portion for contact with an electrolyte, said surface portion being limited by said insulator, and means for pressingly engaging said insulator and said electrode at a pressure of greater than about 0.1 kg/mm² at the interface of said insulator and electrode for counteracting electrolyte penetration into said interface.

26. The transducer of claim 25, wherein said means effect a predetermined and substantially constant pressure of contact between said electrode and said insulator in an area near the electrolyte-contacting end of said interface.

27. The transducer of claim 26, wherein said means includes tensioning means capable of storing mechanical energy and for causing an essentially constant force to act upon said electrode and said insulator at said area.

28. The transducer of claim 25, wherein said insulating means comprises a solid and creep-resistant material.

29. The transducer of claim 25, wherein said pressure of contact between said electrode and said insulator is at least about 0.5 kg/mm².

30. The transducer of claim 25, wherein said pressure of contact between said electrode and said insulator is up to about 95% of the strength of the insulator.

31. The transducer of claim 25, wherein said insulator has a creep modulus of at least 14 kg/mm².

32. The transducer of claim 25, wherein said insulator and electrode are arranged essentially coaxially, said insulator surrounding said electrode over at least the area of the surface portions thereof not intended for exposure to electrolyte.

33. The transducer of claim 32, wherein said interface between said electrode and said insulator has a substantially circular annular plan end portion for contact with said electrolyte, and said pressure of contact between said electrode and said insulator is sealingly effective at least in the vicinity of said end portion.

34. The transducer of claim 25, wherein said electrode has an external frustro-conical section and said insulator has a complementally shaped internal section and is arranged around said electrode so as to form a frustro-conical interface therewith, and wherein tensioning means is provided for generating a substantially constant force of interaction at said frusto-conical interface.

35. The transducer of claim 25, wherein said transducer further comprises a chamber portion for receiving said electrolyte, and wherein said at least one electrode is arranged substantially at the center of the radial cross-section of said chamber portion and has electroanalytically effective surface portion for contact with the electrolyte, said insulator being in a generally coaxial arrangement around said at least one electrode, and comprising another electrode in a generally coaxial arrangement around said insulator and having a recessed part, a member capable of being displaced in a generally axial direction within the recessed part of said another electrode, and a spring operationally connected with said displaceable member, said at least one electrode and said insulator each having a contact face for a mutually sealing engagement, said displaceable member forcing said spring means against said at least one electrode for maintaining substantially constant pressure between said at least one electrode and said insulator in at least a portion of said interface.

36. An amperometric cell for the quantitative determination of the concentration of a component in a fluid comprising an electroanalytical transducer comprising insulating means including an insulator, at least one electrode having an electroanalytically effective surface portion for contact with an electrolyte, said surface portion being limited by said insulator, and means for pressingly engaging said insulator and said electrode at the interface of the electrode and insulator at a pressure of greater than about 0.1 kg/mm² for counteracting electrolyte penetration into said interface between said insulator and said electrode, said cell comprising an electrolyte receiving container portion, a working electrode, a counter electrode and an insulator in contact with said working electrode, said insulating means including a solid creep-resistant material and said insulator contacting said working electrode at a predetermined and substantially constant pressure so as to limit and counteract entry of electrolyte into the interface between said working electrode and said insulator when said cell is operated.

37. The cell of claim 36, wherein said cell is operative to quantitatively analyze oxygen in a liquid or gaseous medium, wherein said electrolyte-receiving container portion is closed against said medium by means of a membrane that is permeable for oxygen.

38. An electroanalytical transducer comprising an electrolyte, a chamber portion for receiving said electrolyte, a first electrode arranged substantially at the center of the radial cross-section of said chamber portion and having an electroanalytically effective surface portion for contact with the electrolyte, insulating means including an insulator in a generally coaxial arrangement around said first electrode and a second electrode in a generally coaxial arrangement around said insulator and having a recessed part, a member capable of being displaced in a generally axial direction within the recessed part of said second electrode, and a spring operationally connected with said displaceable member, said first electrode and said insulator each having a contact face for a mutually sealing engagement, said displaceable member forcing said spring means against said first electrode for pressingly engaging said first electrode and said insulator and maintaining sealingly effective pressure between said first electrode and said insulator in at least a portion of said interface.

39. The transducer recited in claim 38, wherein the insulating means comprises a creep-resistant material and the sealingly effective pressure is at least about 0.1 kg/mm².

* * * * *

UNITED STATES PATENT AND TRADEMARK OFFICE
CERTIFICATE OF CORRECTION

PATENT NO. : 4,096,047
DATED : June 20, 1978
INVENTOR(S) : John Martin Hale and Eugen Weber It is certified that error appears in the above-identified patent and that said Letters Patent are hereby corrected as shown below:

Column 1, line 41, change "deflect" to --defect--.

Column 5, line 46, after "poly" insert -- - --.

Column 11, line 13, change "magnitude" to --magnitudes--.

Column 11, line 31, change "chlorde" to --chloride--.

Column 12, line 22, change "capillary" to --capillarity--.

Column 12, line 37, after "(~500 ergs/cm$^2$)" delete --and--.

Column 13, line 2, after "(5)" insert -- : --.

UNITED STATES PATENT AND TRADEMARK OFFICE
CERTIFICATE OF CORRECTION

PATENT NO. : 4,096,047
DATED : June 20, 1978
INVENTOR(S) : John Martin Hale and Eugen Weber It is certified that error appears in the above-identified patent and that said Letters Patent are hereby corrected as shown below:

Column 13, lines 4-5, change

"$W_t = \gamma_{1w} + \gamma_{2w} - \gamma_{12} - (1 - \theta)(\gamma_{1A} + \gamma_{2A}) + (P)$
$(x)$" to --$W_t = \gamma_{1w} + \gamma_{2w} - \gamma_{12} - (1 - \theta)(\gamma_{1A} + \gamma_{2A}) + (P)(x)$--.

Column 15, line 35, after "has" insert --said--.

Signed and Sealed this

Nineteenth Day of December 1978

[SEAL]

Attest:

RUTH C. MASON
*Attesting Officer*

DONALD W. BANNER
*Commissioner of Patents and Trademarks*